(12) United States Patent
Brunet

(10) Patent No.: US 7,798,332 B1
(45) Date of Patent: Sep. 21, 2010

(54) NASAL PRONG PROTECTOR

(76) Inventor: Sarah Mary Brunet, 102 Old Orchard Avenue, Cornwall, ON (CA) K6H 2H3

( * ) Notice: Subject to any disclaimer, the term of this patent is extended or adjusted under 35 U.S.C. 154(b) by 0 days.

(21) Appl. No.: 12/704,302

(22) Filed: Feb. 11, 2010

(30) Foreign Application Priority Data

Mar. 24, 2009 (CA) .................................. 2659912

(51) Int. Cl.
*B65D 85/00* (2006.01)
(52) U.S. Cl. .................. 206/570; 206/477; 206/485; 206/364
(58) Field of Classification Search .................. 206/570, 206/571, 363, 364, 370, 437, 477, 480, 482, 206/485
See application file for complete search history.

(56) References Cited

U.S. PATENT DOCUMENTS

| 4,332,322 | A | * | 6/1982 | Jaeschke et al. | ............. | 206/364 |
| 4,386,642 | A | * | 6/1983 | Durbin | ........................ | 190/110 |
| 5,375,717 | A | * | 12/1994 | Roshdy | ....................... | 206/476 |
| 5,441,152 | A | * | 8/1995 | Estes | ........................... | 206/570 |
| 2008/0121554 | A1 | * | 5/2008 | Townsend | .................... | 206/570 |

* cited by examiner

*Primary Examiner*—Jacob K Ackun, Jr.
(74) *Attorney, Agent, or Firm*—Lang Michener LLP

(57) ABSTRACT

The invention consists of a prong protector for use with a nasal cannula, the nasal cannula having a body portion, a pair of nasal prongs extending from the body portion, and first and second supply tubes extending from opposite ends of the body portion. The prong protector includes a housing having an interior surface, for receiving the body portion of the nasal cannula thereon, and first and second sidewalls extending from said interior surface and a cover operatively attached to said housing for defining an open configuration and a closed configuration. The first and second sidewalls have an indented portion along a top edge for receiving the first and second supply tubes therein, such that, in use, the first and second supply tubes extend outside of said housing. The prong protector further includes restraining means for substantially preventing movement of the body portion within said housing.

20 Claims, 4 Drawing Sheets

NASAL PRONG PROTECTOR

FIELD OF THE INVENTION

The present invention relates to the field of nasal cannulas and in particular, a prong protector for use with a nasal cannula.

BACKGROUND OF THE INVENTION

Nasal cannulas are used to deliver supplemental oxygen to users in need of oxygen, generally at flow rates lower than that of an oxygen mask. A nasal cannula is often used on patients who could benefit from oxygen therapy, but do not require oxygen to self-respirate. A common use of the nasal cannula is for oxygen therapy provided to elderly patients suffering from strokes, or other conditions, where vasoconstriction could be especially detrimental to their present condition. Other applications include treating sleep apnea and providing respiratory assistance to patients.

A nasal cannula typically includes a pair of prongs extending from a generally tubular body portion and a pair of supply tubes attached to opposite ends of the body portion. Oxygen is supplied through the supply tubes and to the prongs which are positioned in a patient's nostrils. The supply tubes typically extend behind the ears of the patient to hold the nasal cannula in place during use. Oxygen may be supplied by an oxygen tank, a portable oxygen generator, or a direct line from a wall connection in a hospital.

A problem exists in maintaining the sanitary use of nasal cannulas. In general, when a patient leaves the bedside, the nasal cannula is removed and reinserted when the patient returns. When a patient removes the nasal cannula, for example to use the washroom, the cannula is often left on the bed or a nearby table. As can be appreciated, these surfaces are often unsanitary and can be contaminated by food, a patient's waste. The patient is generally unaware of this and upon returning to the bedside, places the nasal cannula back in the nostrils. Other problems may arise when the cannula is accidentally dropped on the floor, for example, when switching tubing from a portable oxygen generator. Either the nasal cannula has to be replaced, or as often happens, the unsanitary cannula continues to be used.

There is a need in the art for a device which protects the nasal cannula, and more specifically, the prongs of the cannula, when it is dropped on the floor or otherwise placed in unsanitary conditions. There is a further need for such a device which is easy to use, especially for elderly patients, or those with arthritic hands, and can be applied without the aid of a nurse or other caregiver.

SUMMARY OF THE INVENTION

According to one embodiment of the present invention, there is provided a prong protector for use with a nasal cannula, the nasal cannula having a body portion, a pair of nasal prongs extending from the body portion, and first and second supply tubes extending from opposite ends of the body portion, the prong protector comprising a housing having an interior surface, for receiving the body portion of the nasal cannula thereon, and first and second sidewalls extending from the interior surface, a cover operatively attached to the housing for defining an open configuration and a closed configuration; the first and second sidewalls having an indented portion along a top edge for receiving the first and second supply tubes therein, such that, in use, the first and second supply tubes extend outside of the housing; and, restraining means substantially preventing movement of the body portion within the housing.

According to one aspect of the present invention, the indented portion is sized smaller than a diameter of the supply tubes such that when the cover is in the closed configuration, the tubes are compressed between the cover and the indented portion, thereby preventing movement of the body portion within the housing.

According to another aspect of the present invention, the restraining means comprises two or more protrusions extending from the interior surface, the protrusions positioned to receive a portion of the nasal cannula, in compressing relationship, therebetween.

According to another aspect of the present invention, the protrusions are positioned to receive the pair of nasal prongs, in compressing relationship, therebetween.

According to another aspect of the present invention, wherein the protrusions are positioned to receive a portion of the first and second supply tubes, in compressing relationship, therebetween.

According to another aspect of the present invention, wherein the restraining means comprises an internal frame structure shaped and dimensioned to surround at least a portion of the body portion on the surface.

According to another aspect of the present invention, further comprising at least one ventilation opening on the housing.

According to another aspect of the present invention, wherein the housing is manufactured from sterilizable plastics material.

According to another aspect of the present invention, wherein the cover is hingedly attached to the housing, and further comprises a latch for holding the cover in the closed configuration.

According to another aspect of the present invention, wherein the cover and the housing are arranged in a friction fit relationship.

According to another embodiment of the present invention, there is provided a kit comprising a nasal cannula having a body portion, a pair of nasal prongs extending from the body portion, and first and second supply tubes extending from opposite ends of the body portion; and, a prong protector comprising a housing having an interior surface, for receiving the body portion of the nasal cannula thereon, and first and second sidewalls extending from the interior surface; a cover operatively attached to the housing for defining an open configuration and a closed configuration; the first and second sidewalls having an indented portion along a top edge for receiving the first and second supply tubes therein, such that, in use, the first and second supply tubes extend outside of the housing; and, restraining means substantially preventing movement of the body portion within the housing.

The prong protector provided in the aforementioned kit may include all features and elements of the prong protector described in an embodiment of the present invention.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying drawings, the latter of which is briefly described hereinbelow.

BRIEF DESCRIPTION OF THE DRAWINGS

The invention will now be described in more detail, by way of example only, with reference to the accompanying drawings, in which like numbers refer to like elements, wherein.

DETAILED DESCRIPTION OF THE PREFERRED EMBODIMENTS

Figure 1A:
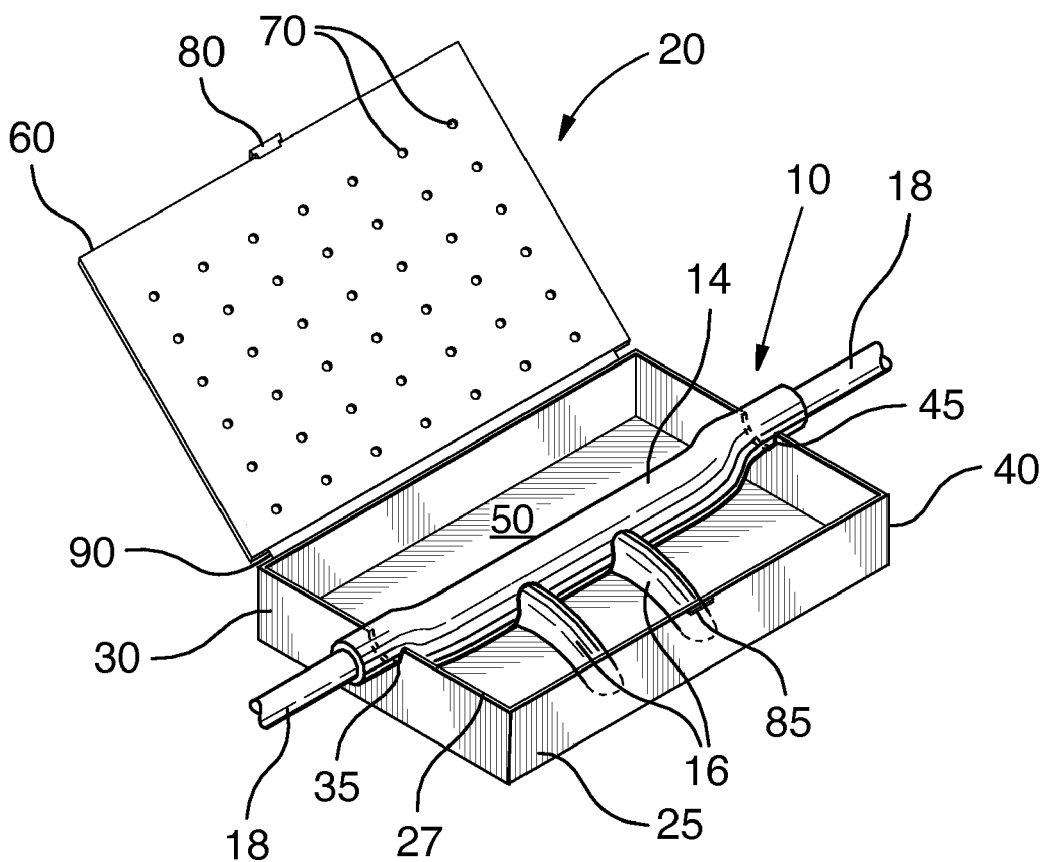
FIG. 1A is perspective view of a prong protector according to a first embodiment of the present invention.
Figure 1B:
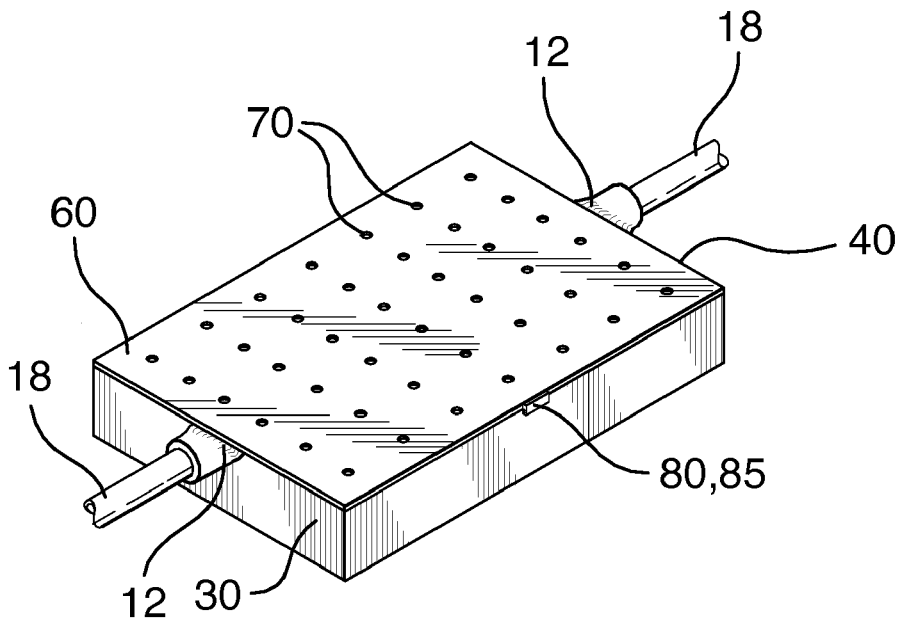
FIG. 1B is a perspective view of the prong protector of FIG. 1A in a closed position.

Referring now to FIGS. 1A and 1B, there is shown a prong protector 20 for use with a nasal cannula 10 according to a first embodiment of the present invention. The nasal cannula 10 is a well known prior art device generally used to deliver supplemental oxygen to a patient, although other uses are known as well. Exemplified in FIG. 1A, the nasal cannula 10 includes a main body portion 14, a pair of nasal prongs 16 extending from the main body portion 14 and first and second supply tubes 18 extending from the main body portion 14, generally at opposite ends thereof. In use, the supply tubes 18 may extend behind a patient's ears (not shown) to support the nasal prongs 16 in position. Other modes of holding the nasal prongs 16 in the nostrils (not shown) of a patient are well known in the art. As the prong protector 20 is chiefly concerned with providing a sanitary enclosure for the main body portion 14 and the nasal prongs 16, other features and elements of nasal cannula 10 which are well known in the art are not further described.

According to the first embodiment, the prong protector 20 comprises a housing 25 having a first sidewall 30 and a second sidewall 40. The first sidewall 30 has a first indented portion 35 extending into the first sidewall 30 from a top edge 27 of housing 25. Likewise, the second sidewall 40 has a second indented portion 45 extending into the second sidewall 40 from the top edge 27. Inside the housing 25, a surface 50 is provided for receiving at least the main body portion 14 of the nasal cannula 10 thereon. A cover 60 is operatively attached to the housing 25 to define an open configuration, as shown in FIG. 1A, and a closed configuration, as shown in FIG. 1B, for the prong protector 20.

The first indented portion 35 and the second indented portion 45 are sized smaller than a diameter of the supply tubes 18 such that when the cover 60 is in the closed configuration of FIG. 1B, the supply tubes 18 are compressed proximate a tube compression region 12, between the cover 60 and the respective indented portion 35 or 45. The supply tubes 18 thus extend outside of the housing 25, but are restrained at the tube compression region 12. As such, the sizing of the first indented portion 35 and the second indented portion 45 form a restraining means for substantially preventing movement of the main body portion 14 within the housing 25. As will be appreciated by those skilled in the art, the first indented portion 35 and the second indented portion 45 are sized and shaped such that the tube compression region 12 is minimally compressed so as to prevent permanent deformation of the tubes 18, or cause any other changes in the structure and properties of the tubes 18 which would alter the flow rate of air through the tubes 18 when in use by a patient.

Optionally, one or more ventilation openings 70 are provided in the cover 60 to allow prevent bacterial growth within the prong protector 20. Preferably, the surface 50 is further provided with an anti-bacterial coating. A latch means, such as catch 80 and detent 85 may also be provided to maintain the cover 60 in the closed configuration. Such catch 80 and detent 85 type mechanisms are easy to operate and can be open and closed by a person with arthritic problems without significant difficulty. Preferably, a hinge 90 is provided to allow rotation of the cover 60 from the open configuration of FIG. 1A to the closed configuration of FIG. 1B.

In use of the first embodiment, a patient requiring leave from the bedside, or any other place which necessitates the removal of the prongs 16 from the nasal cavities (not shown) will position the main body portion 14, and the prongs 16 on the surface 50 within the housing 25. Subsequently, the tubes 18 can be pressed into place in the first indented portion 35 and the second indented portion 45 to secure the nasal cannula 10 in place. The cover 60 can then be closed and catch 80 will be retained by detent 85. Upon returning, the catch 80 is easily disengaged from detent 85 and the nasal cannula 10 subsequently removed from the prong protector 20. The prong protector 20 may then be stored in a convenient location close to the patient for future use.

Figure 2A:
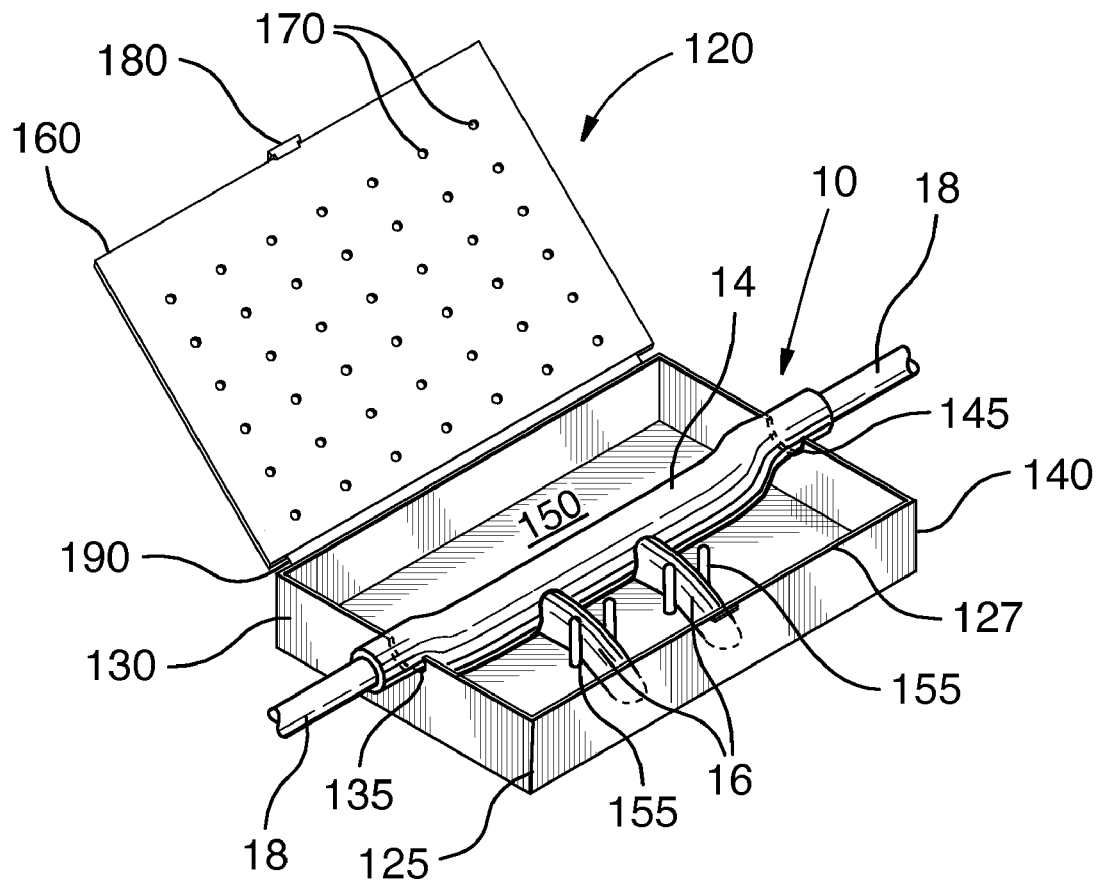
FIG. 2A is a perspective view of a prong protector according to a second embodiment of the present invention.
Figure 2B:
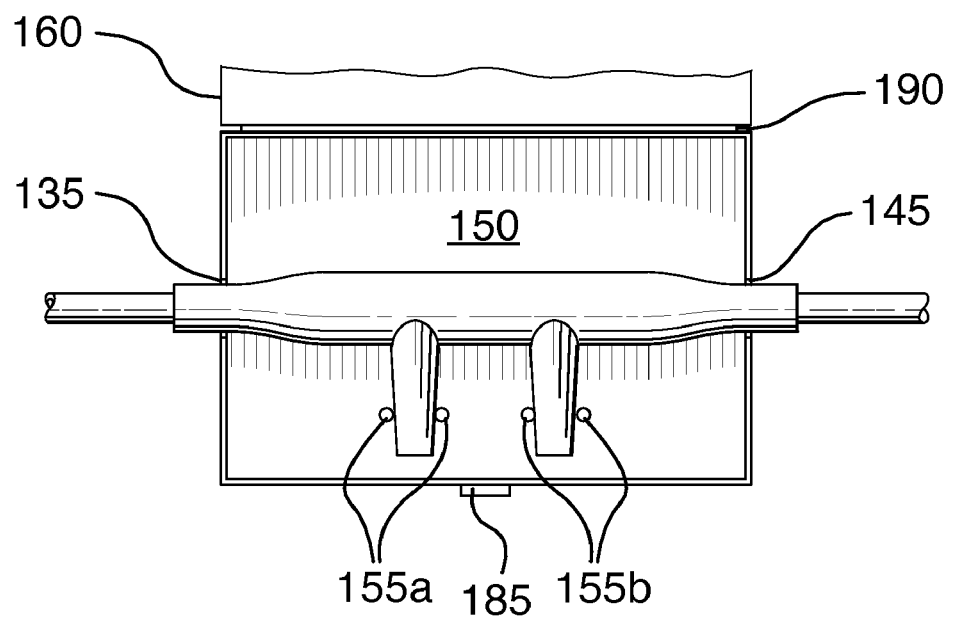
FIG. 2B is a top view of the prong protector of FIG. 2A.

Referring now to FIGS. 2A and 2B, a prong protector 120 according to a second embodiment of the present invention is shown. Like elements from the first embodiment are numbered correspondingly, in the 100's and are not further described in detail, unless required for ease of understanding the prong protector 120 of the second embodiment. A lid 160, hinge 190, optional ventilation openings 170, catch 180 and detent 185 operate as correspondingly numbered elements in the first embodiment and are thus not described in detail. According to the second embodiment, depressed from a top edge 127 of housing 125 are a first indented portion 135 and a second indented portion 145 extending into a first sidewall 130 and a second sidewall 140 respectively. Preferably, the first indented portion 135 and the second indented portion 145 are preferably sized larger than tubes 18 such that the tubes 18 may freely rest therein, and extend outside of the housing 125. Provided on an internal surface 150 of the prong protector 120 according to the second embodiment, are one or more protrusions 155 extending from the internal surface 150 and positioned to retrain movement of the nasal cannula 10. Preferably four protrusions 155 are provided, extending from the internal surface 150 and positioned to receive the pair of nasal prongs 16 therebetween. The four protrusions 155 are preferably provided in two pairs, 155a and 155b, each of which surrounds one of the nasal prongs 16. The nasal prongs 16 are compressed between the respective protrusions 155 to hold the nasal prongs 16 in a compressing relationship therebetween, thus restraining the nasal cannula 10 and substantially preventing movement of the main body portion 14 within the housing 125.

In use of the second embodiment, the patient positions the nasal prongs 16 between the protrusions 155 as shown in FIG. 2A, ensuring that tubes 18 extend outside the housing 125 through the first indented portion 135 and the second indented portion 145. The lid 160 is then closed and the prongs 16 of the nasal cannula 10 are protected within the prong protector 120.

Figure 3A:
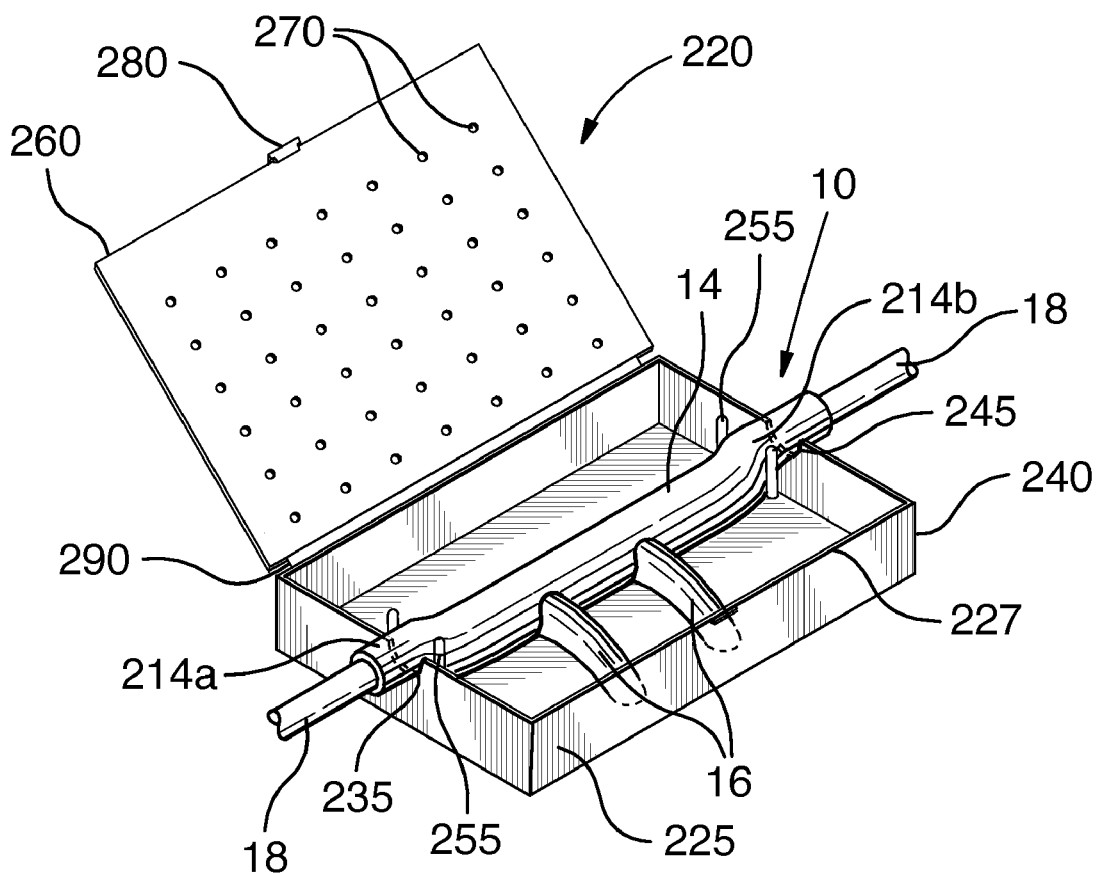
FIG. 3A is a perspective view of a prong protector according to a third embodiment of the present invention.
Figure 3B:
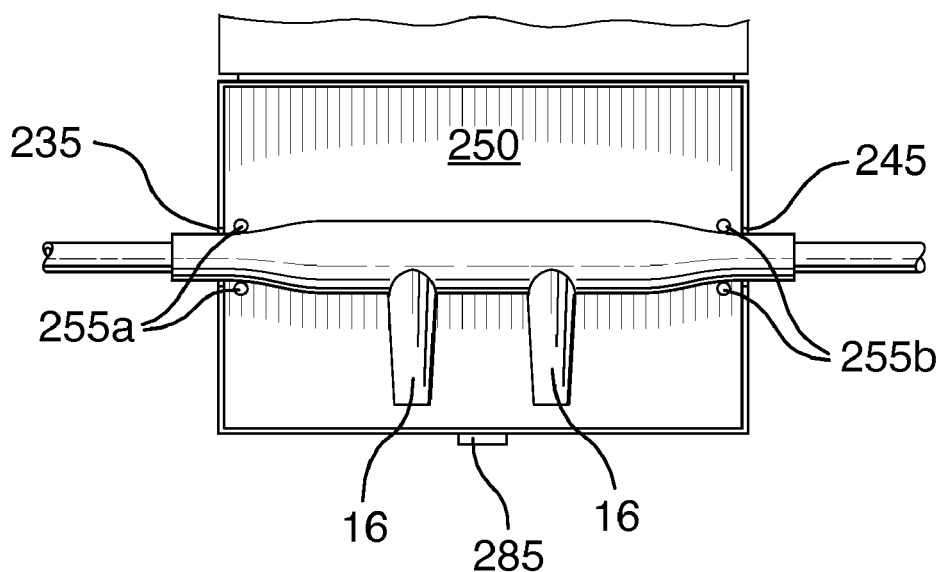
FIG. 3B is a top view of the prong protector of FIG. 3A.

Referring now to FIGS. 3A and 3B, a prong protector 220 according to a third embodiment of the present invention is shown. Like elements from the first and second embodiments are numbered correspondingly, in the 200's and are not further described in detail, unless required for ease of understanding the prong protector 220 of the third embodiment. According to the third embodiment, depressed from a top edge 227 of housing 225 are a first indented portion 235 and a second indented portion 245 extending into a first sidewall 230 and a second sidewall 240 respectively. The first indented portion 235 and the second indented portion 245 are sized such that the tubes 18 may freely rest therein, and extend outside of the housing 225. Provided on an internal surface 250 of the prong protector 220 according to the third embodiment, are one or more, and preferably four protrusions 255 extending from the internal surface 250 and positioned to receive a portion of the main body portion 14, proximate tubes 18 therebetween. The four protrusions 255 are preferably provided in two pairs, 255a and 255b, each of which surrounds a respective end portion 214a and 214b of the main body portion 14, proximate tubes 18. The end portions 214a and 214b are compressed between the respective protrusions 255a and 255b to hold the nasal prongs in a compressing relationship therebetween, thus restraining the nasal cannula 10 and substantially preventing movement of the main body portion 14 within the housing 225.

In use of the third embodiment, the patient positions the end portions 214a and 214b between the protrusions 255a and 255b as shown in FIG. 2A, ensuring that tubes 18 extend outside the housing 225 through the first indented portion 235 and the second indented portion 245. The lid 260 is then closed and the prongs 16 of the nasal cannula 10 are protected within the prong protector 220.

Figure 4A:
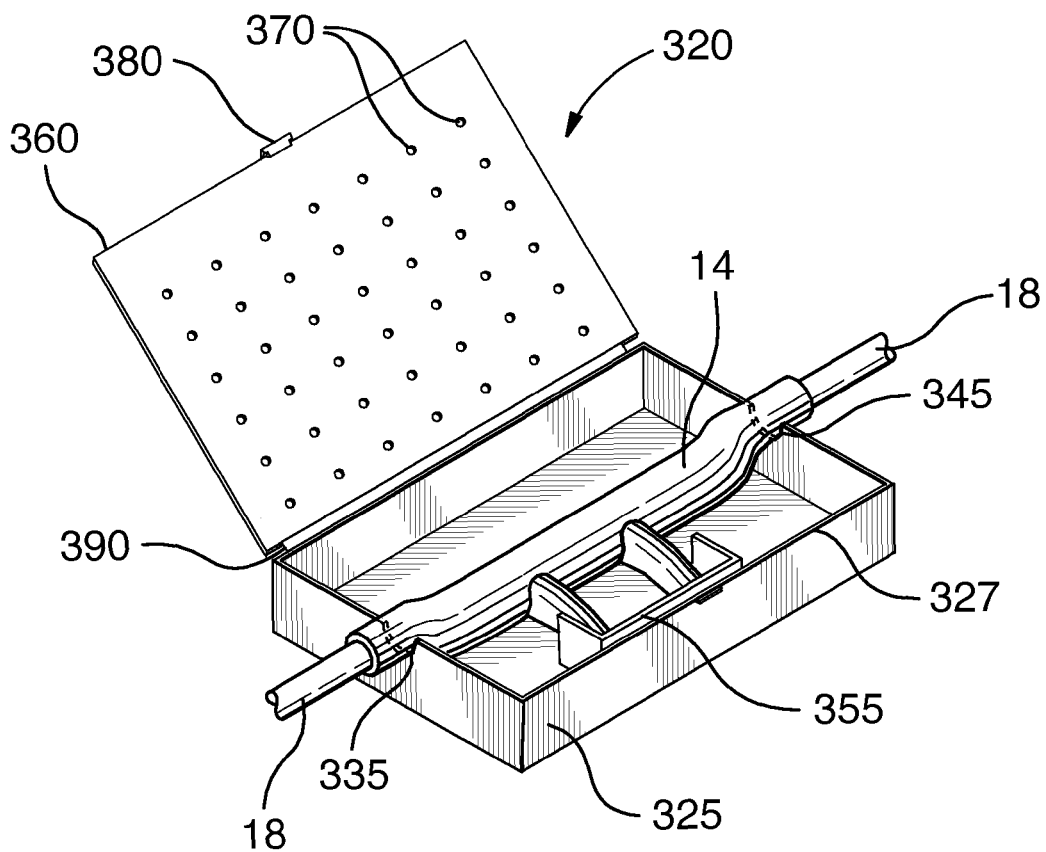
FIG. 4A is a perspective view of a prong protector according to a third embodiment of the present invention; and, FIG. 4B is a top view of the prong protector of FIG. 4A.
Figure 4B:
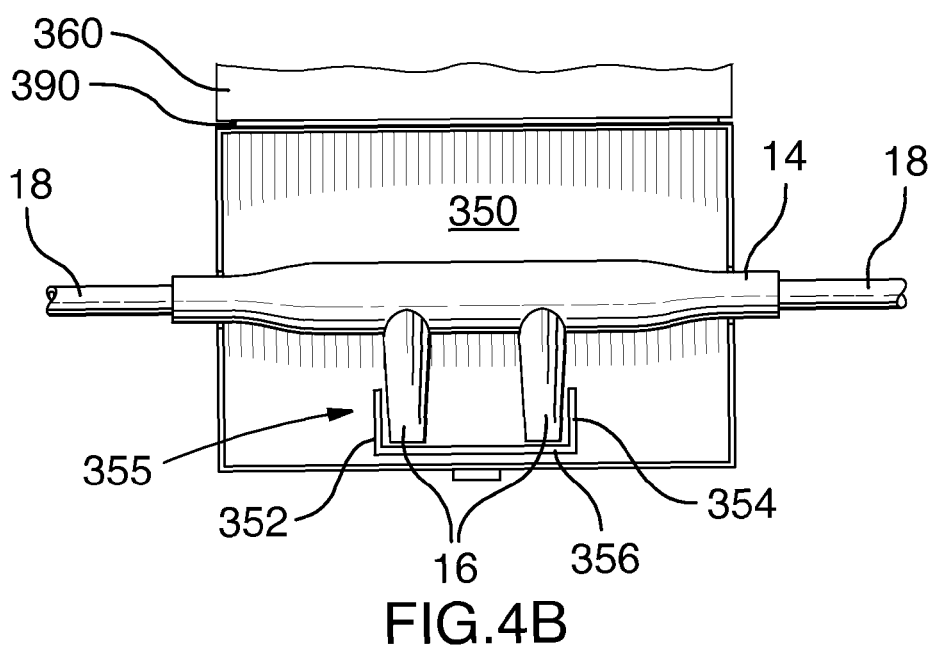

Referring now to FIGS. 4A and 4B, a prong protector 320 according to a fourth embodiment of the present invention is shown. Like elements from the first and second embodiments are numbered correspondingly, in the 300's and are not further described in detail, unless required for ease of understanding the prong protector 320 of the fourth embodiment. According to the fourth embodiment, depressed from a top edge 327 of housing 325 are a first indented portion 335 and a second indented portion 345 extending into a first sidewall 330 and a second sidewall 340 respectively. The first indented portion 335 and the second indented portion 345 are sized such that the tubes 18 may freely rest therein, and extend outside of the housing 325. Provided on an internal surface 350 of the prong protector 320 according to the fourth embodiment, is an internal frame structure 355. The internal frame structure 390 preferably comprises a first side portion 352 and a second side portion 354, interconnected by a front portion 356. The internal frame structure 355 is sized and shaped to receive the nasal prongs 16 between the first side portion 352 and the second side portion 354 in a close fitting relationship to thereby position and substantially restrain the nasal cannula 10 against movement within the housing 325.

In use of the fourth embodiment, the patient positions the nasal prongs 16 within the internal frame structure 390, between the first side portion 352 and the second side portion 354, ensuring that tubes 18 extend outside the housing 325 through the first indented portion 335 and the second indented portion 345. The lid 360 is then closed and the prongs 16 of the nasal cannula 10 are protected within the prong protector 320.

Now described, with reference to the first embodiment, but applicable to any of the embodiments herein disclosed, is a kit which may be provided comprising the nasal cannula 10 and the prong protector 20, along with instructions for a patient on how to position the nasal cannula 10 within the prong protector 20. The prong protector 20 is optionally reusable, such that when replacing the nasal cannula, the user may keep the prong protector 20 for subsequent use.

Optionally, the prong protector 20 may be manufactured from a sterilizable plastics material such that the prong protector 20 may be repeatedly sterilized and reused. Any method of manufacture known in the art may be employed to produce the prong protector 20. Preferably, the prong protector 20 is molded to include all internal features herein described.

This concludes the description of the presently preferred embodiments of the invention. The foregoing description has been presented for the purpose of illustration and is not intended to be exhaustive or to limit the invention to the precise form disclosed. Many modifications and variations are possible in light of the above teaching and will be apparent to those skilled in the art. It is intended the scope of the invention be limited not by this description but by the claims that follow. Various other modifications and alterations may be used in the design and manufacture of the prong protector according to the present invention without departing from the spirit and scope of the invention, which is limited only by the accompanying claims. For example, any type of anti-bacterial coating known to those skilled in the art may be applied to any surface or portion of the prong protector to prevent the growth of bacteria when the prong protector is in a closed configuration. Furthermore, other coatings or surface treatments may be applied, which, for example, allow the prong protector to be kept sanitary and cleansed more easily. It is also contemplated that other mechanisms and/or elements for closing the prong protector, other than the cover, hinge and catch/detent described hereinabove may be used. For example, a removable, friction fit cover which is pressed into place or a slidable cover which may be operated by sliding the cover horizontally. The ventilation openings may alternatively be provided on other surfaces of the housing, such as the sides, front, back or a base portion, rather than on the cover. These alternates are provided for example only and are not to be considered limiting.

Furthermore, the protrusions of the second and third embodiments may be positioned on any portion of the surface of the prong protector and arranged to prevent movement of the body portion within the housing, for example. Any number of protrusions may also be used. The internal frame structure of the fourth embodiment may comprise any such frame structure arranged to surround, or otherwise hold in place, any portion of the nasal cannula within the housing to act as a restraining means for substantially preventing movement of the body portion of the nasal cannula within the housing. In addition, combinations of the various embodiments are also contemplated. For example, a prong protector may include both an internal frame structure and protrusions positioned to receive a portion of the cannula therebetween.

The embodiments of the invention in which an exclusive property or privilege is claimed are defined as follows:

1. A prong protector for use with a nasal cannula, the nasal cannula having a body portion, a pair of nasal prongs extending from the body portion, and first and second supply tubes extending from opposite ends of the body portion, said prong protector comprising:

i. a housing having an interior surface, for receiving the body portion of the nasal cannula thereon, and first and second sidewalls extending from said interior surface;
ii. a cover operatively attached to said housing for defining an open configuration and a closed configuration;
iii. said first and second sidewalls having an indented portion along a top edge for receiving the first and second supply tubes therein, such that, in use, the first and second supply tubes extend outside of said housing; and,
iv. restraining means substantially preventing movement of the body portion within said housing.

2. A prong protector according to claim 1, wherein said indented portion is sized smaller than a diameter of the first and second supply tubes such that when said cover is in said closed configuration, the tubes are compressed between said cover and said indented portion, thereby preventing movement of the body portion within said housing.

3. A prong protector according to claim 1, wherein said restraining means comprises two or more protrusions extending from said interior surface, said protrusions positioned to receive a portion of the nasal cannula, in compressing relationship, therebetween.

4. A prong protector according to claim 3, wherein said two or more protrusions comprise two pairs of protrusions, each pair positioned to receive a respective one of the pair of nasal prongs therebetween.

5. A prong protector according to claim 3, wherein said protrusions are positioned to receive a portion of the first and second supply tubes therebetween.

6. A prong protector according to claim 1, wherein said restraining means comprises an internal frame structure shaped and dimensioned to surround at least a portion of the body portion on said interior surface.

7. A prong protector according to claim 1, further comprising at least one ventilation opening on said housing.

8. A prong protector according to claim 1, wherein said housing is manufactured from sterilizable plastics material.

9. A prong protector according to claim 1, wherein said cover is hingedly attached to said housing, and further comprises a latch for holding said cover in said closed configuration.

10. A prong protector according to claim 1, wherein said cover and said housing are arranged in a friction fit relationship.

11. A kit comprising:
a nasal cannula having a body portion, a pair of nasal prongs extending from the body portion, and first and second supply tubes extending from opposite ends of the body portion; and,
a prong protector comprising:
i. a housing having an interior surface, for receiving the body portion of the nasal cannula thereon, and first and second sidewalls extending from said interior surface;
ii. a cover operatively attached to said housing for defining an open configuration and a closed configuration;
iii. said first and second sidewalls having an indented portion along a top edge for receiving the first and second supply tubes therein, such that, in use, the first and second supply tubes extend outside of said housing; and,
iv. restraining means substantially preventing movement of the body portion within said housing.

12. A kit according to claim 11, wherein said indented portion is sized smaller than a diameter of the first and second supply tubes such that when said cover is in said closed configuration, the tubes are compressed between said cover and said indented portion, thereby preventing movement of the body portion within said housing.

13. A kit according to claim 11, wherein said restraining means comprises two or more protrusions extending from said interior surface, said protrusions positioned to receive a portion of the nasal cannula, in compressing relationship, therebetween.

14. A kit according to claim 13, wherein said two or more protrusions comprise two pairs of protrusions, each pair positioned to receive a respective one of the pair of nasal prongs therebetween.

15. A kit according to claim 13, wherein said protrusions are positioned to receive a portion of the first and second supply tubes therebetween.

16. A kit according to claim 11, wherein said restraining means comprises an internal frame structure shaped and dimensioned to surround at least a portion of the body portion on said interior surface.

17. A kit according to claim 11, further comprising at least one ventilation opening on said housing.

18. A kit according to claim 11, wherein said housing is manufactured from sterilizable plastics material.

19. A kit according to claim 11, wherein said cover is hingedly attached to said housing, and further comprises a latch for holding said cover in said closed configuration.

20. A kit according to claim 11, wherein said cover and said housing are arranged in a friction fit relationship.

* * * * *